United States Patent [19]

Bockow

[11] Patent Number: 5,709,855
[45] Date of Patent: Jan. 20, 1998

[54] COMPOSITIONS OF SPIRULINA ALGAE AND OMEGA FATTY ACIDS FOR TREATMENT OF INFLAMMATION AND PAIN

[76] Inventor: Barry L Bockow, 16122 - 8th Ave. SW., Seattle, Wash. 98166

[21] Appl. No.: 538,992

[22] Filed: Sep. 22, 1995

[51] Int. Cl.$^6$ .................. A61K 35/80; A61K 31/20; A61K 31/60; A61K 31/19

[52] U.S. Cl. .................. 424/93.7; 514/560; 514/165; 514/570

[58] Field of Search .................. 514/560, 165, 514/570; 424/93.7

[56] References Cited

U.S. PATENT DOCUMENTS 5,137,828  8/1992  Robinson et al. .................. 435/296
5,223,285  6/1993  DeMichele et al. .................. 426/72

*Primary Examiner*—William R.A. Jarvis
*Attorney, Agent, or Firm*—Seed and Berry

[57] ABSTRACT

A composition for preventing or treating inflammation and/or pain by topical administration are disclosed. The composition contains an omega fatty acid in combination with spirulina. Preferably, the omega fatty acid is a mixture of omega-3 fatty acids and omega-6 fatty acids. Omega-3 fatty acids include eicosapentaenoic acid and docosahexanoic acid, and omega-6 fatty acids include gamma-linolenic acid and dihomo-gamma-linolenic acid. The composition may further include pharmaceutically acceptable carriers or diluents, vitamins A and E, and a cyclooxygenase inhibitor such as methyl salicylate.

18 Claims, No Drawings

COMPOSITIONS OF SPIRULINA ALGAE AND OMEGA FATTY ACIDS FOR TREATMENT OF INFLAMMATION AND PAIN

TECHNICAL FIELD

The present invention relates generally to compositions and methods for preventing and/or treating inflammation and pain in patients and, more specifically, to compositions containing omega fatty acids and spirulina and to methods for their administration.

BACKGROUND OF THE INVENTION

The prevention or inhibition of inflammation and pain is of significant concern to medical professionals, particularly in the case of patients afflicted with arthritis and other musculoskeletal ailments, including sports-related injuries.

The immune system is a protective network that enables the body to ward off disease. A mechanism by which this occurs is through the initiation of an inflammatory response. In attempting to heal areas of injury, the body sometimes mounts an overly aggressive immune response. This "hyper" immune response is the cause of a group of illnesses known as "autoimmune diseases" which include rheumatoid arthritis. The immune response is often associated with increased blood flow and increased vascular permeability. This causes the release of white blood cells, macrophages, platelets and other cellular elements to the surrounding tissues. These cells are the harbingers of inflammation.

Prostaglandins are a family of compounds which have been identified as playing a significant role in inflammation. Their biosynthesis is triggered by the release of arachidonic acid, a preliminary event in the immune response. Prostaglandins are produced throughout the body and are derived from enzymatic action on a common substrate, arachidonic acid. The first step in prostaglandin synthesis is the oxygenation of arachidonic acid by the enzyme cyclooxygenase. The oxygenated prostaglandin precursors are subject to further enzymatic processes which provide the various members of the prostaglandin family.

Arachidonic acid is an essential fatty acid consisting of twenty carbon atoms and containing four carbon-carbon double bonds. By virtue of the position of the carbon-carbon double bond at the methyl (omega) end of the hydrocarbon chain, it is classified as an omega-6 fatty acid. A closely related family of fatty acids are the omega-3 fatty acids. In addition to double bond position, omega-6 and omega-3 fatty acids may also be distinguished by their origins. The precursors to these fatty acids are derived from botanical and/or marine plants which are in turn further metabolized in animals to provide the long chain polyunsaturated acids. Omega-6 fatty acids may be found predominantly in land animals, while omega-3 fatty acids are abundant in fish.

Closely related in structure and function to the prostaglandins are a family of compounds known as leukotrienes. Leukotrienes are also derived from arachidonic acid metabolism, but through the lipoxygenase pathway. Like prostaglandins, leukotrienes exhibit inflammatory properties. It is believed that inhibition of the enzymatic pathways which yield prostaglandins and leukotrienes would result in decreased production of such compounds, with a consequent reduction in their inflammatory effects To this end, omega fatty acids are known to inhibit production of prostaglandins and leukotrienes, and are effective inhibitors of inflammation. Oral administration of omega fatty acids, however, has limited effectiveness and suffers from several drawbacks. Fatty acids that are taken orally are subject to gastrointestinal absorption and metabolism. To compensate for the reduction of active compound reaching the targeted body region, increased dosages of fatty acids are required. In addition, oral administration of fatty acids is not tissue specific and the dosage is distributed throughout the body. Because these omega fatty acids affect biological processes beyond prostaglandin synthesis, side effects associated with oral administration have been observed. For example, omega fatty acids are known to interfere with normal platelet function, and oral administration generally results in the increased danger of bleeding (Rogers et al., *Atherosclerosis* 63:137–43, 1987). The effect of omega fatty acids on platelet function also adversely affects capillary fragility.

Most effective medications for treatment of inflammatory conditions such as arthritis are administered either orally or parenterally and thus have the potential of producing significant systemic side effects. For example, non-steroidal anti-inflammatory drugs often produce such undesirable effects as gastric irritation, renal insufficiency, bleeding disorders, and congestive heart failure. Particularly in the geriatric population, the very group most often requiring long-term effective treatment for arthritis, these side effects often preclude successful treatment. In the elderly population, both hepatic and renal function are often compromised, thereby potentially increasing the toxic effects of medications. In addition, reduction of serum albumin in the elderly can adversely alter the pharmacodynamics of drugs (D. S. Chutka, J. Evans, et al., *Mayo Clinic Proceedings* 70:685–93, 1995).

Despite the great need to inhibit inflammation and pain, current therapeutic options and preventive measures have serious limitations. As mentioned above, many patients are unable to take oral compounds because of systemic or local side effects. Furthermore, current topical compounds are not effectively absorbed transcutaneously.

Accordingly, there is a need in the art for compositions that can be administered topically to a desired area of a patient's body and that can be absorbed transcutaneously to effectively modulate immune response and prevent, inhibit, or provide treatment for inflammation and/or pain. The present invention fulfills these needs, and provides further related advantages.

SUMMARY OF THE INVENTION

Briefly stated, the present invention discloses methods and compositions for topical administration to prevent or treat inflammation and/or pain in a warm-blooded animal. In one embodiment, a composition comprising an omega fatty acid and spirulina is disclosed. The composition contains a therapeutically effective amount of the omega fatty acid and spirulina in combination with one or more acceptable carriers and/or diluents. In a preferred embodiment, the omega fatty acid is a mixture of an omega-3 fatty acid and an omega-6 fatty acid.

In a further embodiment, a method is disclosed for preventing or treating inflammation by topically administering a composition of this invention to a warm-blooded animal in need thereof. In a preferred embodiment, the composition is topically administered to an area over the joint, tendon, bursa, muscle, or periarticular structure of the animal. In another embodiment, the composition is topically applied to an animal suffering from musculoskeletal pain of multiple etiologies, including both inflammatory and non-inflammatory conditions, as well as sports-related injuries.

These and other aspects of this invention will become evident upon reference to the following detailed description.

DETAILED DESCRIPTION OF THE INVENTION

The present invention is generally directed to a composition and a method for preventing or treating inflammation and/or pain in a warm-blooded animal, including a human and a domesticated animal, such as a dog and a horse (hereinafter referred to as a patient). More specifically, this invention discloses a composition containing an omega fatty acid and the blue-green algae spirulina, as well as a method for administration of the composition. In the context of this invention, it has been found that spirulina exerts a synergistic effect in combination with an omega fatty acid.

In addition to an omega fatty acid and spirulina, the composition of the present invention also contains a pharmaceutically acceptable carrier or diluent. Optional ingredients of the composition further include a cyclooxygenase inhibitor, squalene, and vitamins A and E.

Although not intending to be limited to the following theory, it is believed that the composition of the present invention effectively inhibits the syntheses of biochemicals which are ultimately responsible for inflammation. These biochemicals include prostaglandins and leukotrienes. The omega fatty acid of the composition of the present invention inhibits the above-mentioned prostaglandin and leukotriene syntheses through interference with the cyclooxygenase and lipoxygenase pathways, respectively.

In addition, the composition of this invention is also believed to inhibit interleukin production. Interleukins are soluble, immuno-enhancing glycoproteins produced by T-lymphocytes, and have been commonly used as immuno stimulants to restore or bolster immune response. Interleukin-2, for example, is a potent mediator of the inflammatory response. Therapeutic measures that lower interleukin levels are associated with a decreased inflammatory response and often improved clinical outcome. Competitive inhibition by the omega fatty acid of the present invention is believed to interfere with the utilization of arachidonic acid in both cyclooxygenase and lipoxygenase pathways, and renders the production of prostaglandins and leukotrienes largely inoperative. The same competitive inhibition principle is believed to apply to the diminution of interleukin production as well.

Fatty acids are a class of organic compounds that are characterized by a long hydrocarbon chain terminating with a carboxylic acid group. Fatty acids have a carboxyl end and a methyl (i.e., "omega") end. Omega-3 fatty acids are derived from marine sources, while omega-6 fatty acids are derived from botanical sources. In addition to the difference in their origins, these omega fatty acids may be distinguished based on their structural characteristics.

Omega-3 fatty acids are a family of polyunsaturated fatty acids where the unsaturated carbon most distant from the carboxyl group is the third carbon from the methyl terminus. Omega-3 fatty acids have the following general formula:

where R is a saturated or unsaturated, substituted or unsubstituted, branched or straight chain alkyl group having from 1 to 20 carbon atoms. Preferably, R is an unsaturated straight chain alkyl having from 13 to 17 carbon atoms (i.e., an omega-3 fatty acid having from 18 to 22 total carbon atoms), and containing from 2 to 6 carbon-carbon double bonds. In a preferred embodiment, the compositions of the present invention comprise omega-3 fatty acids which contain 20 carbon atoms with 5 carbon-carbon double bonds, or 22 carbon atoms with 6 carbon-carbon double bonds, including (but not limited to) eicosapentaenoic acid ("EPA") and docosahexaenoic acid ("DHA"):

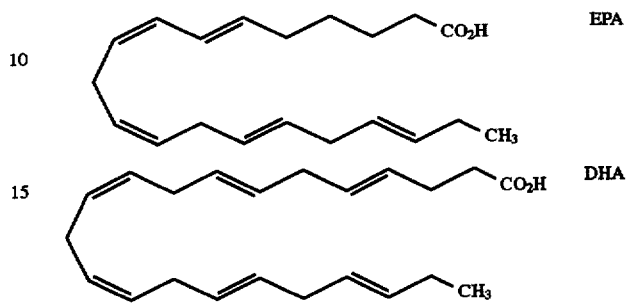

Similarly, omega-6 fatty acids are a family of unsaturated fatty acids where the unsaturated carbon most distant from the carboxyl group is the sixth carbon from the methyl terminus. Omega-6 fatty acids have the following general formula:

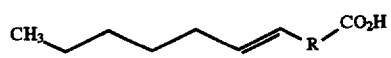

where R is a saturated or unsaturated, substituted or unsubstituted, branched or straight chain alkyl group having from 1 to 20 carbon atoms. Preferably, R is an unsaturated straight chain alkyl having from 10 to 14 carbon atoms (i.e., an omega-6 fatty acid having from 18 to 22 total carbon atoms), and containing from 2 to 6 carbon-carbon double bonds. In a preferred embodiment, the compositions of the present invention comprise omega-6 fatty acids which contain 18 carbon atoms with 3 carbon-carbon double bonds, or 20 carbon atoms with 4 carbon-carbon double bonds, including (but not limited to) gamma-linolenic acid ("GLA") and dihomo-gamma-linolenic acid ("DHGLA"):

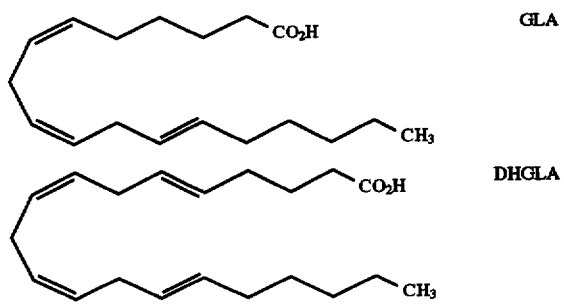

The omega fatty acid of the present invention may comprise an omega-3 fatty acid, an omega-6 fatty acid, a mixture of two or more omega-3 fatty acids, a mixture of two or more omega-6 fatty acids, or a mixture of one or more omega-3 and one or more omega-6 fatty acids.

In addition to the omega fatty acid, the compositions of the present invention contain the blue-green algae spirulina. Spirulina contains a mixture of biologically active proteins, amino acids, lipids, vitamins and cofactors (see "Chemical Analysis of Spirulina," *Food from Sunlight*, C. Hills and H. Nakamura, World Hunger Research Project, University of the Trees Press, 336, 1978). Spirulina belongs to the group cyanobacteria (blue-green algae) and has been used as a food for over a thousand years (O. Ciferri, *Microbiol. Rev.*

47:551–78, 1983). It has been suggested that, in addition to its general health benefits, it is effective in reducing hypercholesterolemia (N. Nakaga, Y. Homma and Y. Goto, *Nutr. Rep. Int.* 37:1329–1337, 1988). Controlled studies have shown that spirulina is capable of preventing the formation of malignant tumors in hamsters challenged with buccal application of a potent carcinogen (J. Schwartz, G. Shklar, S. Reid and D. Trickier, *Nutritional Cancer* 11:127–34, 1988). Spirulina has also been found to have a radioprotective effect on mouse bone marrow cells (P. Qishen, B. J. Guo and A. Kolman, *Toxicology Letter* 48:165–69, 1989). Furthermore, researchers have suggested that dietary intake of spirulina enhances the immune response (O. Hayashi, T. Katoch and Y. Okuwaki, *J. Nutr. Sci. Vitaminol.* 40:431–41, 1994).

Although the compositions of this invention are disclosed as being a combination of an omega fatty acid and spirulina, it should be understood that, upon identification of the active component(s) of spirulina, such component(s) may be employed as an equivalent substitute for spirulina. Accordingly, as used herein, the term "spirulina" is intended to encompass both the blue-green algae itself, as well as any active extract, isolate or component thereof.

The composition of the present invention may optionally comprise a cyclooxygenase inhibitor. Cyclooxygenase inhibitors of the compositions of the present invention include any compound which effectively inhibits cyclooxygenase, including (but not limited to) acetylating and non-acetylating inhibitors. Cyclooxygenase inhibitors which acetylate cyclooxygenase (i.e., "acetylating inhibitors") include acetylsalicylic acid (aspirin) and methyl salicylic acid, as well as salts thereof. Cyclooxygenase inhibitors which do not acetylate cyclooxygenase (i.e., "non-acetylating inhibitors") include (but are not limited to) salicylates such as salicylic acid, salicylsalicylic acid, trilisate, and disalcid, and salts thereof. Other cyclooxygenase inhibitors include naproxen, piroxicam, indomethacin, sulindac, meclofenamate, diflunisal, tolmetin, etodolac, ketorolac, diclofenac, ibuprofen, fenoprofen, ketoprofen and nabumetone. When present in the composition, a cyclooxygenase inhibitor is included in amounts sufficient to prevent or treat inflammation and/or pain in a patient when administered to the patient in combination with the omega fatty acid and spirulina.

The composition of the present invention may also contain vitamin E. Anti-oxidants such as vitamin E have been shown to enhance cellular immune function, act as free radical scavengers, and block other metabolic processes that are deleterious to healthy tissues. A recent review article discusses the role of antioxidants in the prevention of atherosclerosis by the same mechanisms (*Postgraduate Medicine* 98(1):175–84, 1995). The article cites the role of vitamin E in blocking the oxidation of LDL cholesterol and preventing the formation of foam cells that would trigger an inflammatory reaction and the production of an atheromatous plaque. Vitamin E is present in the composition in amounts sufficient to block the deleterious effects of the above mentioned metabolic processes in combination with the omega fatty acid and spirulina.

The composition of the present invention may also contain other additional optional ingredients including, but not limited to, vitamin A, Carbomer 2001 (a carboxyvinyl polymer thickening agent), squalene, aloe vera, and capcacin. Both vitamins A and E provide composition stability.

The composition of the present invention possesses both lipophilic and hydrophilic properties. The lipophilic moeity enhances absorption through the stratum corneum, which is primarily a lipid layer, and through the subcutaneous tissues, which are primarily aqueous (see, e.g., Berti and Lipsky, "Transcutaneous Drug Delivery: A Practical Review," *Mayo Clinic Prodeeding* 70:581–86, 1995).

For purposes of administration, the composition of the present invention may be formulated in any suitable manner for application to a surface (such as the skin or mucosal tissue) of the patient's body which is to be treated. Such formulations contain effective amounts of the omega fatty acid and spirulina, as well as one or more pharmaceutically acceptable carriers or diluents. More specifically, the formulations of the present invention may be administrated in the form of liquids containing acceptable diluents such as deionized water and alcohol, or may be administered as suspensions, emulsions, gels or creams containing acceptable diluents or carriers to impart the desired texture, consistency, viscosity and appearance. Such acceptable diluents and carriers are familiar to those skilled in the art and include (but are not limited to) fatty alcohols, fatty acids, fatty esters, organic and inorganic bases, steroid esters, triglyceride esters, phospholipids such as lecithin and cephalin, polyhydric alcohol esters, hydrophobic lanolin derivatives, hydrocarbon oils, cocoa butter waxes, silicon oils, preserving agents, pH balancers and cellulose derivatives. One skilled in the art may further formulate the omega fatty acid and spirulina in an appropriate manner, and in accordance with accepted practices, such as those disclosed in *Remington's Pharmaceutical Sciences*, Gennaro, Ed., Mack Publishing Co., Easton, Pa. 1990 (which is incorporated herein by reference in its entirety).

The omega fatty acid and spirulina are present in the composition in an amount sufficient to prevent or treat inflammation and/or pain in a patient when administered topically to the patient. When formulated for such administration, the omega fatty acids may be present in an amount ranging from 1% to 65% by weight (based on the total weight of the formulation), more preferably from 2% to 40% by weight, and most preferably from 3% to 30%. Similarly, spirulina may be present in an amount ranging from 0.1% to 8% by weight, more preferably from 2% to 7% by weight, and most preferably from 3% to 6%.

Further optional ingredients include a cyclooxygenase inhibitor optionally present in an amount ranging from 3% to 25% by weight, vitamin A optionally present in an amount ranging from 0.5% to 3% by weight, squalene optionally present in an amount ranging from 5% to 20% by weight, Carbomer 2001 (2% solution) optionally present in an amount ranging from 5% to 15% by weight, aloe vera optionally present in an amount ranging from 0.2% to 5% by weight, and capcacin optionally present in an amount ranging from 0.1% to 1% by weight. Example 1 illustrates representative formulations of the composition of the present invention for topical applications.

The composition of the present invention may be used to prevent or treat a variety of musculoskeletal conditions, both inflammatory and non-inflammatory in nature, and acute, subacute or chronic presentation. For example, the composition may be used in the treatment of both the early and late stages of inflammatory arthritis, as well as non-infectious inflammatory arthropathy such as rheumatoid arthritis, bursitis, tendinitis, soft tissue injuries, Sjögren's syndrome, systemic lupus erythematous, psoriatic arthritis, gout and other crystalline arthropathies, capsulitis, carpal tunnel syndrome, myositis, polymyalgia, rheumatica, synovitis and Reiter's syndrome. The compositions of this invention may also be used in the prevention or treatment of erosive osteoarthritis.

With respect to the prevention or treatment of pain, the compositions of this invention may be topically applied to the patient as an analgesic to prevent or treat acute or chronic pain including lower back pain or sciatica, as well as foot pain such as heel pain, heel spurs, fasciities, metatarsalgia and Achilles tendinitis. The compositions of this invention also have utility in the prevention or treatment of pain associated with osteoarthritis.

Furthermore, the compositions may be administered for dental applications. For example, the compositions of this invention are useful in preventing inflammation after tooth extraction or for treating various forms of gum disease. More specifically, after a periodontist performs gum surgery, an amount of the composition in the form of a liquid, gel or cream may be applied directly to the wound, or may be used to bathe the inflamed tissues as a rinse.

Alternatively, in the prevention or treatment of musculoskeletal conditions, the composition may be applied daily in the form of a liquid, cream or gel directly on inflamed tissue. For example, the liquid, cream or gel may be applied generously to the affected area from 1 to 4 times daily and gently massage into the skin until fully absorbed. Following application, an occlusive dressing may be optionally applied for 4 to 10 hours to enhance efficacy. Absorption of the composition can be further enhanced by phoresis, ultrasound and other physical therapy modalities.

The following examples are provided for purposes of illustration, not limitation.

EXAMPLE 1

Representative Compositions

The following Formulations I through X are representative compositions of the present invention formulated for topical application. In the following formulations, the omega-3 fatty acids, eicosapentaenoic acid and docosahexaenoic acid, are referred to as "EPA" and "DHA," respectively, and the omega-6 fatty acids, gamma-linolenic acid and dihomo-gamma-linolenic acid are referred to as "GLA" and "DHGLA," respectively. "Carbomer 2001" is a trade name for a carboxyvinyl polymer thickening agent. The compositions may be formulated by mixing the following ingredients according to the weight percentages shown.

| | % by weight |
|---|---|
| Formulation I | |
| EPA | 0.1–20 |
| DHA | 0.1–15 |
| GLA and/or DHGLA | 0.1–20 |
| Spirulina | 0.1–7 |
| Methyl Salicylate | 3–25 |
| Vitamin A | 0.5–3 |
| Vitamin E | 0.5–3 |
| Squalene | 5–20 |
| Carbomer 2001 (2% solution) | 5–15 |
| Water and other inert ingredients | 30–60 |
| Formulation II | |
| EPA | 0.1–20 |
| DHA | 0.1–15 |
| GLA and/or DHGLA | 0.1–20 |
| Spirulina | 0.1–7 |
| Methyl Salicylate | 3–25 |
| Vitamin A | 0.5–3 |
| Vitamin E | 0.5–3 |
| Squalene | 5–20 |
| Carbomer 2001 (2% solution) | 5–15 |
| Aloe Vera | 0.2–5 |
| Water and other inert ingredients | 30–60 |

| | % by weight |
|---|---|
| Formulation III | |
| EPA | 0.1–20 |
| DHA | 0.1–15 |
| GLA and/or DHGLA | 0.1–20 |
| Spirulina | 0.1–7 |
| Methyl Salicylate | 3–25 |
| Vitamin A | 0.5–3 |
| Vitamin E | 0.5–3 |
| Squalene | 5–20 |
| Carbomer 2001 (2% solution) | 5–15 |
| Capcacin | 0.1–1 |
| Aloe Vera | 0.2–5 |
| Water and other inert ingredients | 30–60 |
| Formulation IV | |
| EPA | 0.1–15 |
| DHA | 0.1–20 |
| GLA and/or DHGLA | 0.1–20 |
| Spirulina | 0.1–7 |
| Methyl Salicylate | 3–25 |
| Vitamin A | 0.5–3 |
| Vitamin E | 0.5–3 |
| Squalene | 5–20 |
| Carbomer 2001 (2% solution) | 5–15 |
| Water and other inert ingredients | 30–60 |
| Formulation V | |
| EPA | 0.1–15 |
| DHA | 0.1–20 |
| GLA and/or DHGLA | 0.1–20 |
| Spirulina | 0.1–7 |
| Methyl Salicylate | 3–25 |
| Vitamin A | 0.5–3 |
| Vitamin E | 0.5–3 |
| Squalene | 5–20 |
| Aloe Vera | 0.2–5 |
| Carbomer 2001 (2% solution) | 5–15 |
| Water and other inert ingredients | 30–60 |
| Formulation VI | |
| EPA | 0.1–15 |
| DHA | 0.1–20 |
| GLA and/or DHGLA | 0.1–20 |
| Spirulina | 0.1–7 |
| Methyl Salicylate | 3–25 |
| Vitamin A | 0.5–3 |
| Vitamin E | 0.5–3 |
| Squalene | 5–20 |
| Carbomer 2001 (2% solution) | 5–15 |
| Capcacin | 0.1–1 |
| Aloe Vera | 0.2–5 |
| Water and other inert ingredients | 30–60 |
| Formulation VII | |
| EPA | 0.1–20 |
| DHA | 0.1–15 |
| GLA and/or DHGLA | 0.1–20 |
| Spirulina | 0.1–7 |
| Vitamin A | 0.5–3 |
| Vitamin E | 0.5–3 |
| Squalene | 5–20 |
| Carbomer 2001 (2% solution) | 5–15 |
| Water and other inert ingredients | 30–70 |
| Formulation VIII | |
| EPA | 0.1–20 |
| DHA | 0.1–15 |
| GLA and/or DHGLA | 0.1–20 |
| Spirulina | 0.1–7 |
| Vitamin A | 0.5–3 |
| Vitamin E | 0.5–3 |
| Squalene | 5–20 |
| Carbomer 2001 (2% solution) | 5–15 |
| Aloe Vera | 0.2–5 |
| Water and other inert ingredients | 30–70 |

| | % by weight |
|---|---|
| Formulation IX | |
| EPA | 0.1–20 |
| DHA | 0.1–15 |
| GLA and/or DHGLA | 0.1–20 |
| Spirulina | 0.1–7 |
| Vitamin A | 0.5–3 |
| Vitamin E | 0.5–3 |
| Squalene | 5–20 |
| Carbomer 2001 (2% solution) | 5–15 |
| Capcacin | 0.1–1 |
| Aloe Vera | 0.2–5 |
| Water and other inert ingredients | 30–70 |
| Formulation X | |
| Omega fatty acid | 0.1–20 |
| Spirulina | 0.1–7 |
| Water | (remainder) |

EXAMPLE 2

Inhibition of Pain and Inflammation

The following example illustrates the administration of a representative composition of the present invention to inhibit pain and inflammation.

Two hundred-fifty patients were treated with Formulation II of Example 1 for a period of 6 to 9 months. The diagnoses of the patients included the following conditions: osteoarthritis, rheumatoid arthritis, tendinitis, bursitis, fibromyalgia, autoimmune disorders, chronic fatigue syndrome and sports-related injuries. Of the 250 patients treated, 220 or 88% showed significant and sustained pain relief along with improved quality of daily living. In those patients suffering from an inflammatory condition, inflammation was reduced in the area treated with the composition of this example. With regard to patients suffering from chronic fatigue syndrome, the number of tender points were reduced. No adverse side effects were observed.

EXAMPLE 3

Inhibition of Inflammation

In this experiment, Formulation II of Example 1 was topically applied to 3 horses and 1 dog suffering from a wide range of conditions, including tendinitis, bursitis, myositis, ligamentous and degenerative arthritis. In all cases, inflammation in the treatment area was significantly reduced following topical administration of Formulation II.

From the foregoing, it will be appreciated that, although specific embodiments of this invention have been described herein for the purposes of illustration, various modifications may be made without departing from the spirit and scope of the invention. Accordingly, the invention is not limited except by the appended claims.

I claim:

1. A composition comprising an omega fatty acid, a spirulina blue-green algae, and a pharmaceutically acceptable carrier or diluent.

2. The composition of claim 1 wherein the omega fatty acid is an omega-3 fatty acid.

3. The composition of claim 1 wherein the omega fatty acid is an omega-6 fatty acid.

4. The composition of claim 1 wherein the omega fatty acid is a mixture of an omega-3 fatty acid and an omega-6 fatty acid.

5. The composition of claim 2 wherein the omega-3 fatty acid is selected from the group consisting of eicosapentaenoic acid, docosahexanoic acid, and mixtures thereof.

6. The composition of claim 3 wherein the omega-6 fatty acid is selected from the group consisting of gamma-linolenic acid, dihomo-gamma-linolenic acid, and mixtures thereof.

7. The composition of claim 1 further comprising a cyclooxygenase inhibitor.

8. The composition of claim 7 wherein the cyclooxygenase inhibitor is selected from the group consisting of methyl salicylic acid, acetylsalicylic acid, salicylsalicylic acid, salicyclic acid, trilisate, disalcid, and salts thereof.

9. The composition of claim 7 wherein the cyclooxygenase inhibitor is selected from the group consisting of naproxen, piroxicam, indomethacin, sulindac, meclofenamate, difusinal, tolmetin, ibuprofen, fenoprofen, etodolac, ketorolac, diclofenac, ketoprofen and nabumetone.

10. The composition of claim 1 further comprising vitamin E.

11. The composition of claim 1 further comprising vitamin A.

12. The composition of claim 1 further comprising squalene.

13. The composition of claim 1 wherein the omega fatty acid is present in an amount ranging from 1% to 65% by weight of the composition.

14. The composition of claim 1 wherein the omega fatty acid is present in an amount ranging from 2% to 40% by weight of the composition.

15. The composition of claim 1 wherein the omega fatty acid is present in an amount ranging from 3% to 30% by weight of the composition.

16. The composition of claim 1 wherein the spirulina is present in an amount ranging from 0.1% to 8% by weight of the composition.

17. The composition of claim 1 wherein the spirulina is present in an amount ranging from 2% to 7% by weight of the composition.

18. The composition of claim 1 wherein the spirulina is present in an amount ranging from 3% to 6% by weight of the composition.

* * * * *

UNITED STATES PATENT AND TRADEMARK OFFICE
CERTIFICATE OF CORRECTION

PATENT NO. : 5,709,855
DATED : January 20, 1998
INVENTOR(S) : Barry I. Bockow

It is certified that error appears in the above-identified patent and that said Letters Patent is hereby corrected as shown below:

Title page:

Co-inventor's name has been omitted. Line [76] of patent should read:

Inventors: Barry I. Bockow, 16122 - 8th Ave. S.W., Seattle, Washington 98166 and
Marc D. Erlitz, 4885 Forest Avenue S.E., Mercer Island, Washington 98040

Signed and Sealed this

Fifth Day of September, 2000

Attest:

Attesting Officer

Q. TODD DICKINSON
Director of Patents and Trademarks